United States Patent
Scheibel et al.

(10) Patent No.: US 9,896,648 B2
(45) Date of Patent: Feb. 20, 2018

(54) ETHOXYLATED DIOLS AND COMPOSITIONS CONTAINING ETHOXYLATED DIOLS

(71) Applicant: The Procter & Gamble Company, Cincinnati, OH (US)

(72) Inventors: Jeffrey John Scheibel, Glendale, OH (US); Scott Leroy Cron, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 41 days.

(21) Appl. No.: 15/058,526

(22) Filed: Mar. 2, 2016

(65) Prior Publication Data

US 2017/0253839 A1    Sep. 7, 2017

(51) Int. Cl.
| | |
|---|---|
| C11D 1/02 | (2006.01) |
| C11D 1/72 | (2006.01) |
| C11D 3/43 | (2006.01) |
| C07C 43/13 | (2006.01) |
| C11D 1/29 | (2006.01) |
| C11D 11/00 | (2006.01) |
| C11D 17/00 | (2006.01) |
| C11D 17/04 | (2006.01) |
| C11D 3/20 | (2006.01) |
| C11D 3/37 | (2006.01) |

(52) U.S. Cl.
CPC .............. *C11D 3/43* (2013.01); *C07C 43/135* (2013.01); *C11D 1/29* (2013.01); *C11D 3/2068* (2013.01); *C11D 3/3707* (2013.01); *C11D 11/0017* (2013.01); *C11D 11/0094* (2013.01); *C11D 17/003* (2013.01); *C11D 17/0008* (2013.01); *C11D 17/042* (2013.01); *C11D 17/045* (2013.01)

(58) Field of Classification Search
CPC ........... C11D 1/02; C11D 1/72; C11D 3/2041; C11D 3/43
See application file for complete search history.

(56) References Cited

U.S. PATENT DOCUMENTS

| | | | |
|---|---|---|---|
| 4,175,062 A | * | 11/1979 | Disch ....................... C11D 1/83 510/101 |
| 4,747,977 A | | 5/1988 | Whitehead et al. |
| 4,889,652 A | | 12/1989 | Sullivan et al. |
| 6,323,172 B1 | * | 11/2001 | Trinh ....................... C11D 1/62 510/329 |
| 6,831,048 B2 | | 12/2004 | Kezuka et al. |
| 6,989,072 B2 | | 1/2006 | Catlin et al. |
| 7,220,714 B2 | | 5/2007 | Masuda et al. |
| 8,143,458 B2 | | 3/2012 | Kalagias |
| 8,183,199 B2 | | 12/2012 | Fossum et al. |
| 8,617,417 B2 | | 12/2013 | Inaba et al. |
| 9,165,760 B2 | | 10/2015 | Fu et al. |
| 9,404,071 B2 | | 8/2016 | Labeque et al. |
| 9,624,457 B2 | | 4/2017 | Labeque et al. |
| 2003/0220210 A1 | | 11/2003 | DuVal et al. |
| 2005/0003977 A1 | | 1/2005 | Itano et al. |
| 2010/0313360 A1 | | 12/2010 | Menting et al. |
| 2011/0239377 A1 | | 10/2011 | Fossum et al. |
| 2014/0107008 A1 | | 4/2014 | Fu et al. |
| 2015/0065410 A1 | | 3/2015 | Meier et al. |
| 2016/0355752 A1 | | 12/2016 | Souter et al. |
| 2016/0355753 A1 | | 12/2016 | Gummel et al. |
| 2016/0355754 A1 | | 12/2016 | Somerville-Roberts et al. |
| 2016/0355755 A1 | | 12/2016 | Brooker et al. |
| 2016/0355762 A1 | | 12/2016 | Brooker et al. |
| 2016/0355763 A1 | | 12/2016 | Somerville-Roberts et al. |
| 2016/0355766 A1 | | 12/2016 | Brooker et al. |
| 2016/0355767 A1 | | 12/2016 | Souter et al. |

FOREIGN PATENT DOCUMENTS

| | | |
|---|---|---|
| EP | 1 352 948 A1 | 10/2003 |
| EP | 1 462 514 B1 | 9/2004 |
| EP | 2 368 970 B1 | 6/2015 |
| KR | 20140006661 | 1/2014 |
| WO | WO 93/03129 A1 | 2/1993 |
| WO | WO 97/03172 | 1/1997 |

OTHER PUBLICATIONS

PCT International Search Report for application No. PCT/US2017/015739, dated Apr. 12, 2017, 14 pages.

* cited by examiner

*Primary Examiner* — Brian P Mruk
(74) *Attorney, Agent, or Firm* — Gregory S. Darley-Emerson; Leonard W Lewis; Steven W Miller

(57) ABSTRACT

The present invention relates generally to surfactant and detergent compositions and, more specifically, to surfactant and detergent compositions containing an ethoxylated diol.

11 Claims, No Drawings

ETHOXYLATED DIOLS AND COMPOSITIONS CONTAINING ETHOXYLATED DIOLS

TECHNICAL FIELD

The present invention relates generally to surfactant and detergent compositions and, more specifically, to surfactant and detergent compositions containing an ethoxylated diol.

BACKGROUND

Fluid detergent products, such as liquids, gels, pastes and the like, are preferred by many consumers over solid detergents. Fluid detergent products may contain surfactants, e.g., anionic surfactants, and one or more solvents, in addition to water. Solvents may provide a variety of benefits: solvents may allow for the formulation of anionic surfactant-rich surfactant systems, particularly for compacted fluid detergents; solvents may adjust the viscosity of a formulation; solvents may allow for the formulation of an isotropic and physically stable formulation; and solvents may allow for the formulation of enzymes, polymers, bleach, chelants, and other ingredients that improve cleaning. Solvents may also be used to formulate stable, shippable, anionic surfactant concentrates, which may be combined downstream with other detergent ingredients to form a final detergent product. Also, some fluid detergent forms, such as fluid unit dose articles, may contain high levels of anionic surfactant and high levels of solvent, such as 30% or more solvent by weight of the total formulation.

Known solvents for use in fluid detergent formulations include 1,2-propane diol (p-diol), ethanol, diethylene glycol (DEG), 2-methyl-1,3-propanediol (MPD), dipropylene glycol (DPG), oligamines (e.g., diethylenetriamine (DETA), tetraethylenepentamine (TEPA), and glycerine (which may, for example, be used in fluid unit dose articles). However, these known solvents all have significant disadvantages, particularly if used at increased levels, including cost, formulatability, dissolution rate, solubility/stability of film in certain fluid unit dose articles, and potential adverse effects on cleaning and/or whiteness. Thus, there remains an ongoing need to identify new solvents that may allow for the formulation of increased concentrations of anionic surfactants in fluid detergent compositions, particularly compact fluid detergent compositions and concentrated surfactant pastes, and may address one or more of the disadvantages of known solvents discussed above.

Separately, a long-chain polyether polyol having a molecular weight of more than about 1,200 g/mole and produced by alkoxylating an initiator with an alkylene oxide in the presence of a basic catalyst having at least one cation thereof chelated with a polyoxyethylene-containing compound having a functionality of at least about three is known. Suitable initiator (or starter) compounds include, but are not limited to, $C_1$-$C_{30}$ monols, ethylene glycol, diethylene glycol, triethylene glycol, propylene glycol, 1,3-propanediol, dipropylene glycol, tripropylene glycol, neopentyl glycol, 1,4-butanediol, 1,3-butanediol, 1,2-butanediol, 2,3-butanediol, 1,6-hexanediol, glycerin, trimethylolpropane, trimethylolethane, pentaerythritol, α-methylglucoside, sorbitol, mannitol, hydroxymethylglucoside, hydroxypropylglucoside, sucrose, N,N,N',N'-tetrakis[2-hydroxyethyl or 2-hydroxypropyl]ethylene diamine, 1,4-cyclohexanediol, cyclohexanedimethanol, hydroquinone, resorcinol, and the like. The long-chain polyether polyol may be used to provide a flexible polyurethane foam.

The alkoxylation of 2-methyl-1,3-propanediol is known; ethoxylated as well as propoxylated 2-methyl-1,3-propanediol are known. 1,4-butanediol ethoxylated is also known.

It has been found that the ethoxylated diols of formula (I) provide a better performing solvent in a fluid detergent product. Furthermore, it has been found that the ethoxylated diols of formula (I) perform better than many existing solvents used in detergent formulations and surfactant pastes, such as 1,2-propylene glycol and dipropylene glycol.

SUMMARY

The present disclosure attempts to solve one more of the needs by providing a compound of formula (I)

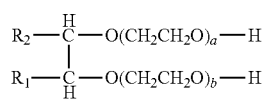

wherein each of $R_1$ and $R_2$ is independently selected from a substituted or unsubstituted, linear or branched, saturated or unsaturated $C_1$-$C_6$ alkyl group, and a+b has an average value of greater than 0 and less than or equal to about 20.

The present disclosure also relates to a composition comprising from about 10% to about 50% by weight of surfactant, a solvent comprising an ethoxylated diol of formula (I)

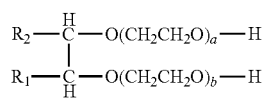

wherein each of $R_1$ and $R_2$ is independently selected from a substituted or unsubstituted, linear or branched, saturated or unsaturated $C_1$-$C_6$ alkyl group, and a+b has an average value of greater than 0 and less than or equal to about 20, an adjunct, and water.

The present disclosure also relates to a composition comprising from about 30% to about 75% by weight of anionic surfactant, a solvent comprising an ethoxylated diol of formula (I)

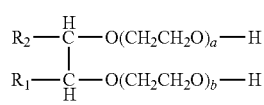

wherein each of $R_1$ and $R_2$ is independently selected from a substituted or unsubstituted, linear or branched, saturated or unsaturated $C_1$-$C_6$ alkyl group, and a+b has an average value of greater than 0 and less than or equal to about 20, and water.

DETAILED DESCRIPTION

Features and benefits of the present invention will become apparent from the following description, which includes examples intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein, the articles including "the," "a" and "an" when used in a claim or in the specification, are understood to mean one or more of what is claimed or described.

As used herein, the terms "include," "includes" and "including" are meant to be non-limiting.

As used herein in reference to Formula (I), the term "average value of a+b" refers to the average moles of ethylene oxide, which is the same as the average degree of ethoxylation. The average value of a+b may be an integer or a fraction.

The term "substantially free of" or "substantially free from" as used herein refers to either the complete absence of an ingredient or a minimal amount thereof merely as impurity or unintended byproduct of another ingredient. A composition that is "substantially free" of/from a component means that the composition comprises less than about 0.5%, 0.25%, 0.1%, 0.05%, or 0.01%, or even 0%, by weight of the composition, of the component.

As used herein the phrase "detergent composition" or "cleaning composition" includes compositions and formulations designed for cleaning soiled material. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, dish washing compositions, hard surface cleaning compositions, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation. The detergent compositions may have a form selected from liquid, powder, single-phase or multi-phase unit dose, pouch, tablet, gel, paste, bar, or flake.

As used herein "butanediol" refers to all structural isomers of the diol, including 1,2-butanediol, 1,3-butanediol, 1,4-butanediol, 1,1-butanediol, 2,2-butanediol, and 2,3-butanediol, as well as stereoisomers of the diol. The term "2,3-butanediol" should be interpreted to include all enantiomeric and diastereomeric forms of the compound, including (R,R), (S,S) and meso forms, in racemic, partially stereoisomerically pure or substantially stereoisomerically pure forms. Similarly, the terms "1,2-butanediol," "1,3-butanediol," "1,4-butanediol," "1,1-butanediol," and "2,2-butanediol" should be interpreted to include any and all enantiomeric and diastereomeric forms of the compound, including (R,R), (S,S) and meso forms, in racemic, partially stereoisomerically pure or substantially stereoisomerically pure forms.

As used herein "hexanediol" refers to all structural isomers of the diol as well as stereoisomers of the diol. The term "3,4-hexanediol" should be interpreted to include all enantiomeric and diastereomeric forms of the compound, including (R,R), (S,S) and meso forms, in racemic, partially stereoisomerically pure or substantially stereoisomerically pure forms.

It should be understood that the terms glycerine, glycerol, and glycerin are synonyms and refer to the following molecule:

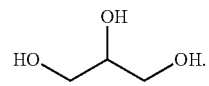

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All cited patents and other documents are, in relevant part, incorporated by reference as if fully restated herein. The citation of any patent or other document is not an admission that the cited patent or other document is prior art with respect to the present invention.

In this description, all concentrations and ratios are on a weight basis of the detergent composition unless otherwise specified.

Ethoxylated Diol

It has been found that the ethoxylated diols of formula (I) provide a better performing solvent in a fluid detergent product. In addition, the ethoxylated diols of formula (I) are more efficient than known solvents.

The disclosure therefore relates to a compound of formula (I)

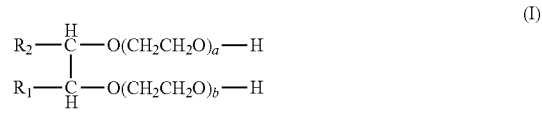

where each of $R_1$ and $R_2$ is independently selected from a substituted or unsubstituted, linear or branched, saturated or unsaturated $C_1$-$C_6$ alkyl group, or a substituted or unsubstituted, linear or branched, saturated or unsaturated $C_1$-$C_3$ alkyl group, or a $C_1$ alkyl group and a+b has an average value of greater than 0, or greater than or equal to 0.1, or greater than or equal to 0.5, or greater than or equal to 1 and less than or equal to about 20, or less than or equal to about 15, or less than or equal to about 10. The average value of a+b may be greater than 0 and less than or equal to about 20.

The compound of formula (I) may be selected from the group consisting of ethoxylated 2,3-butanediol, ethoxylated 3,4-hexanediol, ethoxylated 2,3-hexanediol structural isomers thereof, stereoisomers thereof, and mixtures thereof.

The ethoxylated diol described herein is generally not a single compound as suggested by formula (I), but rather, a mixture of several homologs having varied numbers of total (a+b) ethylene oxide (EO) units per mole of diol. And, the EO units may be bound to the diol molecule in any number of ways across the two branches of the molecule. For example, an ethoxylated diol molecule having a+b=3 (a total of three EOs) has several isomers—all three EOs may be on a single branch (a or b) or two of the three EOs may be on one branch and the third EO may be on the other branch. Ethoxylated diol is a mixture of several homologs, the distribution of which can be measured by gas chromatography (GC) and/or mass spectral analysis (MS).

Also, it is known that in the chemical production process for preparing polyol ethoxylates, such as the ethoxylated diols of formula (I), via standard base catalysis, the polyol starting material may not be 100% free of water. Water may also come in with the base, which is typically a concentrate in water and is stripped prior to adding the ethylene oxide. Drying the polyol/base may be expensive and may take substantial processing time in the reactor. Therefore, it is common practice to dry to a certain level of water (which varies from plant to plant) and proceed with adding ethylene oxide, thereby producing some polyethylene glycol, as an impurity. The amount of polyethylene glycol will vary, based on the level of water present. The amount of polyethylene glycol may be in the range of about 1% to about 5% by weight of the ethoxylated diol of formula (I), or less than about 1% by weight of the ethoxylated diol of formula (I).

2,3-butanediol may be produced by microbial fermentation of carbohydrate containing feedstock. 2,3-butanediol may also be produced by microbial fermentation of biomass from crops such as sugar beet, corn, wheat and sugarcane. However, the cost of these carbohydrate feed stocks is influenced by their value as human food or animal feed and the cultivation of starch or sucrose-producing crops for 2,3-butanediol production is not economically sustainable in all geographies. More recently, methods of producing 2,3-butanediol via the anaerobic fermentation of a substrate comprising carbon monoxide or carbon monoxide and hydrogen by one or more carboxydotrophic acetogenic bacteria have been disclosed by LanzaTech (See U.S. Pat. No. 8,673,603 B2). LanzaTech's gas fermentation process converts carbon-rich waste gases (containing carbon monoxide, carbon dioxide, and/or hydrogen) into biofuels and chemicals, such as 2,3-butanediol.

2,3-butanediol may also be derived by catalytic hydrogenation of sugars, such as glucose, or reduced sugars, such as sorbitol. This process produces a mixture of stereoisomers of 2,3-butanediol as well other structural isomers, such as 1,2-butanediol. Cellulosic sugars may also be a feedstock.

The various processes of making 2,3-butanediol may produce various impurities and/or contaminants. Possible impurities include 2-methyl-1,2-propanediol, 1,2-butanediol, 2-hydroxy-2-butanone, acetoin, butadiene, methyl ethyl ketone, or mixtures thereof. Other impurities may also be present.

Compositions Containing Ethoxylated Diol(s)

The compositions disclosed herein may be dilute or highly concentrated in anionic surfactant (anionic-surfactant rich). The compositions may be premixes (also referred to as surfactant concentrates or pastes) of an anionic surfactant and solvent, which can be used to form finished compositions that are suitable for sale to consumers. The compositions may be compact fluid detergents that are suitable for sale to consumers. The compositions may be dilute fluid detergents that are suitable for sale to consumers.

The disclosure relates to compositions that comprise from about 30% to about 75% by weight of an anionic surfactant, a solvent comprising an ethoxylated diol of formula (I)

where each of $R_1$ and $R_2$ is independently selected from a substituted or unsubstituted, linear or branched, saturated or unsaturated $C_1$-$C_6$ alkyl group, or a substituted or unsubstituted, linear or branched, saturated or unsaturated $C_1$-$C_3$ alkyl group, or a $C_1$ alkyl group and a+b has an average value of greater than 0, or greater than or equal to 0.1, or greater than or equal to 0.5, or greater than or equal to 1 and less than or equal to about 20, or less than or equal to about 15, or less than or equal to about 10, or greater than 0 and less than or equal to about 20, and water. The solvent may further comprise a monoalcohol of formula (II)

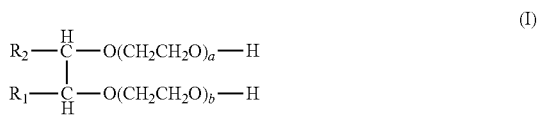

where each of $R_3$, $R_4$, and $R_5$ is independently selected from H or a substituted or unsubstituted, linear or branched $C_1$-$C_6$ alkyl group, glycerine, propoxylated glycerine, ethoxylated glycerine, propylene glycol, diethylene glycol, dipropylene glycol, renewable versions thereof (e.g., renewable propylene glycol, renewable dipropylene glycol), other solvents used in detergent formulation, or mixtures thereof. Suitable monoalcohols include ethanol and cellulosic ethanol.

The composition may be a premix of an anionic surfactant and solvent (also referred to as a surfactant paste or a surfactant concentrate or a concentrated surfactant paste), which can be used to form a finished composition that is suitable for sale to consumers.

The disclosure also relates to compositions that comprise from about 10% to about 50% by weight of surfactant, a solvent comprising an ethoxylated diol of formula (I)

where each of $R_1$ and $R_2$ is independently selected from a substituted or unsubstituted, linear or branched, saturated or unsaturated $C_1$-$C_6$ alkyl group, or a substituted or unsubstituted, linear or branched, saturated or unsaturated $C_1$-$C_3$ alkyl group, or a $C_1$ alkyl group and a+b has an average value of greater than 0, or greater than or equal to 0.1, or greater than or equal to 0.5, or greater than or equal to 1 and less than or equal to about 20, or less than or equal to about 15, or less than or equal to about 10, or greater than 0 and less than or equal to about 20, an adjunct, and water. The solvent may further comprise a monoalcohol of formula (II)

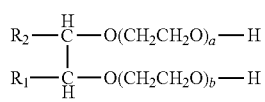

where each of $R_3$, $R_4$, and $R_5$ is independently selected from H or a substituted or unsubstituted, linear or branched $C_1$-$C_6$ alkyl group, glycerine, propoxylated glycerine, ethoxylated glycerine, propylene glycol, diethylene glycol, dipropylene glycol, renewable versions thereof (e.g., renewable propylene glycol, renewable dipropylene glycol), other solvents used in detergent formulation, or mixtures thereof. Suitable monoalcohols include ethanol and cellulosic ethanol.

The composition(s) disclosed herein may comprise from about 2%, or from about 3%, or from about 4%, or from about 6% to about 10%, or to about 12%, or to about 14%, or to about 18%, or to about 20%, or from about 3% to about 18%, or from about 6% to about to about 14% of a compound of formula (I).

The composition(s) disclosed herein may comprise from about 0.05%, or from about 0.1%, or from about 1%, or from about 3%, or from about 5% to about 10%, or to about 12%, or to about 14%, or to about 18%, or to about 20%, or from about 0.1% to about 18%, or from about 3% to about to about 14% of a monoalcohol of formula (II), glycerine, propoxylated glycerine, ethoxylated glycerine, propylene glycol, diethylene glycol, dipropylene glycol, renewable versions thereof (e.g., renewable propylene glycol, renewable dipropylene glycol), other solvents used in detergent formulation, or mixtures thereof.

Surfactant

The compositions disclosed herein may comprise a surfactant selected from the group consisting of anionic surfactants, nonionic surfactants, cationic surfactants, zwitterionic surfactants, amphoteric surfactants, ampholytic surfactants, and mixtures thereof.

Anionic Surfactant

The compositions of the present disclosure may comprise at least about 10%, or at least about 20%, or at least about 30%, or at least about 50%, or at least about 60%, or at least about 70% by weight of an anionic surfactant. The compositions of the present disclosure may comprise less than 100%, or less than 90%, or less than about 85%, or less than about 75%, or less than about 70% by weight of an anionic surfactant. The compositions of the present disclosure may comprise from about 10% to about 50%, or about 20% to about 70%, or about 30% to about 75%, or about 30% to about 65%, or about 35% to about 65%, or about 40% to about 60%, of an anionic surfactant.

The anionic surfactants may exist in an acid form, and the acid form may be neutralized to form a surfactant salt. Typical agents for neutralization include metal counterion bases, such as hydroxides, e.g., NaOH or KOH. Further suitable agents for neutralizing anionic surfactants in their acid forms include ammonia, amines, or alkanolamines. Non-limiting examples of alkanolamines include monoethanolamine, diethanolamine, triethanolamine, and other linear or branched alkanolamines known in the art; suitable alkanolamines include 2-amino-1-propanol, 1-aminopropanol, monoisopropanolamine, or 1-amino-3-propanol. Amine neutralization may be done to a full or partial extent, e.g., part of the anionic surfactant mix may be neutralized with sodium or potassium and part of the anionic surfactant mix may be neutralized with amines or alkanolamines.

Non-limiting examples of suitable anionic surfactants include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. Suitable anionic surfactants may be derived from renewable resources, waste, petroleum, or mixtures thereof. Suitable anionic surfactants may be linear, partially branched, branched, or mixtures thereof.

Alkoxylated alkyl sulfate materials comprise ethoxylated alkyl sulfate surfactants, also known as alkyl ether sulfates or alkyl polyethoxylate sulfates. Examples of ethoxylated alkyl sulfates include water-soluble salts, particularly the alkali metal, ammonium and alkylolammonium salts, of organic sulfuric reaction products having in their molecular structure an alkyl group containing from about 8 to about 30 carbon atoms and a sulfonic acid and its salts. (Included in the term "alkyl" is the alkyl portion of acyl groups. In some examples, the alkyl group contains from about 15 carbon atoms to about 30 carbon atoms. In other examples, the alkyl ether sulfate surfactant may be a mixture of alkyl ether sulfates, said mixture having an average (arithmetic mean) carbon chain length within the range of about 12 to 30 carbon atoms, and in some examples an average carbon chain length of about 12 to 15 carbon atoms, and an average (arithmetic mean) degree of ethoxylation of from about 1 mol to 4 mols of ethylene oxide, and in some examples an average (arithmetic mean) degree of ethoxylation of 1.8 mols of ethylene oxide. In further examples, the alkyl ether sulfate surfactant may have a carbon chain length between about 10 carbon atoms to about 18 carbon atoms, and a degree of ethoxylation of from about 1 to about 6 mols of ethylene oxide. In yet further examples, the alkyl ether sulfate surfactant may contain a peaked ethoxylate distribution.

Non-alkoxylated alkyl sulfates may also be added to the disclosed detergent compositions and used as an anionic surfactant component. Examples of non-alkoxylated, e.g., non-ethoxylated, alkyl sulfate surfactants include those produced by the sulfation of higher $C_8$-$C_{20}$ fatty alcohols. In some examples, primary alkyl sulfate surfactants have the general formula: $ROSO_3^-$ $M^+$, wherein R is typically a linear $C_8$-$C_{20}$ hydrocarbyl group, which may be straight chain or branched chain, and M is a water-solubilizing cation. In some examples, R is a $C_{10}$-$C_{18}$ alkyl, and M is an alkali metal. In other examples, R is a $C_{12}/C_{14}$ alkyl and M is sodium, such as those derived from natural alcohols.

Other useful anionic surfactants can include the alkali metal salts of alkyl benzene sulfonates, in which the alkyl group contains from about 9 to about 15 carbon atoms, in straight chain (linear) or branched chain configuration. In some examples, the alkyl group is linear. Such linear alkylbenzene sulfonates are known as "LAS." In other examples, the linear alkylbenzene sulfonate may have an average number of carbon atoms in the alkyl group of from about 11 to 14. In a specific example, the linear straight chain alkyl benzene sulfonates may have an average number of carbon atoms in the alkyl group of about 11.8 carbon atoms, which may be abbreviated as C11.8 LAS.

Suitable alkyl benzene sulphonate (LAS) may be obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

Another example of a suitable alkyl benzene sulfonate is a modified LAS (MLAS), which is a positional isomer that contains a branch, e.g., a methyl branch, where the aromatic ring is attached to the 2 or 3 position of the alkyl chain.

The anionic surfactant may include a 2-alkyl branched primary alkyl sulfates have 100% branching at the C2 position (C1 is the carbon atom covalently attached to the alkoxylated sulfate moiety). 2-alkyl branched alkyl sulfates and 2-alkyl branched alkyl alkoxy sulfates are generally derived from 2-alkyl branched alcohols (as hydrophobes).

2-alkyl branched alcohols, e.g., 2-alkyl-1-alkanols or 2-alkyl primary alcohols, which are derived from the oxo process, are commercially available from Sasol, e.g., LIAL®, ISALCHEM® (which is prepared from LIAL® alcohols by a fractionation process). C14/C15 branched primary alkyl sulfate are also commercially available, e.g., namely LIAL® 145 sulfate.

The anionic surfactant may include a mid-chain branched anionic surfactant, e.g., a mid-chain branched anionic detersive surfactant, such as, a mid-chain branched alkyl sulphate and/or a mid-chain branched alkyl benzene sulphonate.

Additional suitable anionic surfactants include methyl ester sulfonates, paraffin sulfonates, α-olefin sulfonates, and internal olefin sulfonates.

The compositions disclosed herein may comprise an anionic surfactant selected from the group consisting of linear or branched alkyl benzene sulfonates, linear or branched alkoxylated alkyl sulfates, linear or branched alkyl sulfates, methyl ester sulfonates, paraffin sulfonates, α-olefin sulfonates, internal olefin sulfonates, and mixtures thereof. The compositions disclosed herein may comprise an anionic surfactant selected from the group consisting of linear or branched alkyl benzene sulfonates, linear or branched alkoxylated alkyl sulfates, linear or branched alkyl sulfates, and mixtures thereof. The compositions disclosed herein may comprise a 2-alkyl branched primary alkyl sulfate.

Nonionic Surfactant

The compositions disclosed herein may comprise a nonionic surfactant. Suitable nonionic surfactants include alkoxylated fatty alcohols. The nonionic surfactant may be selected from ethoxylated alcohols and ethoxylated alkyl phenols of the formula $R(OC_2H_4)_nOH$, wherein R is selected from the group consisting of aliphatic hydrocarbon radicals containing from about 8 to about 15 carbon atoms and alkyl phenyl radicals in which the alkyl groups contain from about 8 to about 12 carbon atoms, and the average value of n is from about 5 to about 15.

Other non-limiting examples of nonionic surfactants useful herein include: $C_8$-$C_{18}$ alkyl ethoxylates, such as, NEODOL® nonionic surfactants from Shell; $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols, BA; $C_{14}$-$C_{22}$ mid-chain branched alkyl alkoxylates, $BAE_x$, wherein x is from 1 to 30; alkylpolysaccharides; specifically alkylpolyglycosides; polyhydroxy fatty acid amides; and ether capped poly(oxyalkylated) alcohol surfactants.

Suitable nonionic detersive surfactants also include alkyl polyglucoside and alkyl alkoxylated alcohol. Suitable nonionic surfactants also include those sold under the tradename Lutensol® from BASF.

Cationic Surfactant

The compositions disclosed herein may comprise a cationic surfactant. Non-limiting examples of cationic surfactants include: the quaternary ammonium surfactants, which can have up to 26 carbon atoms include: alkoxylate quaternary ammonium (AQA) surfactants; dimethyl hydroxyethyl quaternary ammonium; dimethyl hydroxyethyl lauryl ammonium chloride; polyamine cationic surfactants; cationic ester surfactants; and amino surfactants, e.g., amido propyldimethyl amine (APA).

Suitable cationic detersive surfactants also include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula:

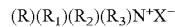

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, for example chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Zwitterionic Surfactant

The compositions disclosed herein may comprise a zwitterionic surfactant. Examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. Suitable examples of zwitterionic surfactants include betaines, including alkyl dimethyl betaine and cocodimethyl amidopropyl betaine, $C_8$ to $C_{18}$ (for example from $C_{12}$ to $C_{18}$) amine oxides, and sulfo and hydroxy betaines, such as N-alkyl-N,N-dimethylammino-1-propane sulfonate where the alkyl group can be $C_8$ to $C_{18}$.

Amphoteric Surfactant

The compositions disclosed herein may comprise an amphoteric surfactant. Examples of amphoteric surfactants include aliphatic derivatives of secondary or tertiary amines, or aliphatic derivatives of heterocyclic secondary and tertiary amines in which the aliphatic radical may be straight or branched-chain and where one of the aliphatic substituents contains at least about 8 carbon atoms, or from about 8 to about 18 carbon atoms, and at least one of the aliphatic substituents contains an anionic water-solubilizing group, e.g. carboxy, sulfonate, sulfate. Suitable amphoteric surfactants also include sarcosinates, glycinates, taurinates, and mixtures thereof.

Adjuncts

The compositions disclosed herein, particularly the dilute and compacted fluid detergents that are suitable for sale to consumers (final products), may comprise adjunct ingredients. The compositions disclosed herein may comprise an adjunct selected from the group consisting of a structurant, a builder, an organic polymeric compound, an enzyme, an enzyme stabilizer, a bleach system, a brightener, a hueing agent, a chelating agent, a suds suppressor, a conditioning agent, a humectant, a perfume, a perfume microcapsule, a filler or carrier, an alkalinity system, a pH control system, a buffer, an alkanolamine, and mixtures thereof.

Enzymes

The compositions described herein may comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a detergent composition, the aforementioned additional enzymes may be present at levels from about 0.00001% to about 2%, from about 0.0001% to about 1% or even from about 0.001% to about 0.5% enzyme protein by weight of the composition. The compositions disclosed herein may comprise from about 0.001% to about 1% by weight of an enzyme (as an adjunct), which may be selected from the group consisting of lipase, amylase, protease, mannanase, cellulase, pectinase, and mixtures thereof.

Enzyme Stabilizing System

The compositions may optionally comprise from about 0.001% to about 10%, or from about 0.005% to about 8%, or from about 0.01% to about 6%, by weight of the composition, of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, chlorine bleach scavengers and mixtures thereof, and are designed to address different stabilization problems depending on the type and physical form of the detergent composition. In the case of aqueous detergent compositions comprising protease, a reversible protease inhibitor, such as a boron compound, including borate, 4-formyl phenylboronic acid, phenylboronic acid and derivatives thereof, or compounds such as calcium formate, sodium formate and 1,2-propane diol may be added to further improve stability.

Builders

The compositions may comprise a builder. Built compositions typically comprise at least about 1% builder, based on the total weight of the composition. Liquid detergent compositions may comprise up to about 10% builder, and in some examples up to about 8% builder, of the total weight of the composition.

Suitable builders include aluminosilicates (e.g., zeolite builders, such as zeolite A, zeolite P, and zeolite MAP), silicates, phosphates, such as polyphosphates (e.g., sodium tri-polyphosphate), especially sodium salts thereof; carbonates, bicarbonates, sesquicarbonates, and carbonate minerals other than sodium carbonate or sesquicarbonate; organic mono-, di-, tri-, and tetracarboxylates, especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. Additional suitable builders may be selected from citric acid, lactic acid, fatty acid, polycarboxylate builders, for example, copolymers of acrylic acid, copolymers of acrylic acid and maleic acid, and copolymers of acrylic acid and/or maleic acid, and other suitable ethylenic monomers with various types of additional functionalities. Alternatively, the composition may be substantially free of builder.

Structurant/Thickeners

Suitable structurants/thickeners include di-benzylidene polyol acetal derivative. The fluid detergent composition may comprise from about 0.01% to about 1% by weight of a dibenzylidene polyol acetal derivative (DBPA), or from about 0.05% to about 0.8%, or from about 0.1% to about 0.6%, or even from about 0.3% to about 0.5%. The DBPA derivative may comprise a dibenzylidene sorbitol acetal derivative (DBS).

Suitable structurants/thickeners also include bacterial cellulose. The fluid detergent composition may comprise from about 0.005% to about 1% by weight of a bacterial cellulose network. The term "bacterial cellulose" encompasses any type of cellulose produced via fermentation of a bacteria of the genus Acetobacter such as CELLULON® by CPKelco U.S. and includes materials referred to popularly as microfibrillated cellulose, reticulated bacterial cellulose, and the like.

Suitable structurants/thickeners also include coated bacterial cellulose. The bacterial cellulose may be at least partially coated with a polymeric thickener. The at least partially coated bacterial cellulose may comprise from about 0.1% to about 5%, or even from about 0.5% to about 3%, by weight of bacterial cellulose; and from about 10% to about 90% by weight of the polymeric thickener. Suitable bacterial cellulose may include the bacterial cellulose described above and suitable polymeric thickeners include: carboxymethylcellulose, cationic hydroxymethylcellulose, and mixtures thereof.

Suitable structurants/thickeners also include cellulose fibers. The composition may comprise from about 0.01 to about 5% by weight of the composition of a cellulosic fiber. The cellulosic fiber may be extracted from vegetables, fruits or wood. Commercially available examples are Avicel® from FMC, Citri-Fi from Fiberstar or Betafib from Cosun. Suitable structurants/thickeners also include non-polymeric crystalline hydroxyl-functional materials. The composition may comprise from about 0.01 to about 1% by weight of the composition of a non-polymeric crystalline, hydroxyl functional structurant. The non-polymeric crystalline, hydroxyl functional structurants generally may comprise a crystallizable glyceride which can be pre-emulsified to aid dispersion into the final fluid detergent composition. The crystallizable glycerides may include hydrogenated castor oil or "HCO" or derivatives thereof, provided that it is capable of crystallizing in the liquid detergent composition.

Suitable structurants/thickeners also include polymeric structuring agents. The compositions may comprise from about 0.01% to about 5% by weight of a naturally derived and/or synthetic polymeric structurant. Examples of naturally derived polymeric structurants of use in the present invention include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. Examples of synthetic polymeric structurants of use in the present invention include: polycarboxylates, polyacrylates, hydrophobically modified ethoxylated urethanes, hydrophobically modified non-ionic polyols and mixtures thereof.

Suitable structurants/thickeners also include di-amido-gellants. The external structuring system may comprise a di-amido gellant having a molecular weight from about 150 g/mol to about 1,500 g/mol, or even from about 500 g/mol to about 900 g/mol. Such di-amido gellants may comprise at least two nitrogen atoms, wherein at least two of said nitrogen atoms form amido functional substitution groups. The amido groups may be different or the same. Non-limiting examples of di-amido gellants are: N,N'-(2S,2'S)-1,1'-(dodecane-1,12-diylbis(azanediyl))bis(3-methyl-1-oxobutane-2,1-diyl)diisonicotinamide; dibenzyl (2S ,2'S)-1,1'-(propane-1,3-diylbis(azanediyl))bis(3-methyl-1- oxobutane-2,1-diyl)dicarbamate; dibenzyl (2S ,2'S)-1,1'-(dodecane-1,12-diylbis(azanediyl))bis(1-oxo-3-phenylpropane-2,1-diyl)dicarbamate.

Polymeric Dispersing Agents

The cleaning composition may comprise one or more polymeric dispersing agents. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The cleaning composition may comprise one or more amphiphilic cleaning polymers such as the compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n=from 20 to 30, and x=from 3 to 8, or sulphated or sulphonated variants thereof.

The cleaning composition may comprise amphiphilic alkoxylated grease cleaning polymers which have balanced hydrophilic and hydrophobic properties such that they remove grease particles from fabrics and surfaces. The amphiphilic alkoxylated grease cleaning polymers may comprise a core structure and a plurality of alkoxylate groups attached to that core structure. These may comprise alkoxylated polyalkylenimines, for example, having an inner polyethylene oxide block and an outer polypropylene oxide block. Such compounds may include, but are not limited to, ethoxylated polyethyleneimine, ethoxylated hexamethylene diamine, and sulfated versions thereof. Polypropoxylated derivatives may also be included. A wide variety of amines and polyalklyeneimines can be alkoxylated to various degrees. A useful example is 600 g/mol polyethyleneimine core ethoxylated to 20 EO groups per NH and is available from BASF. The detergent compositions described herein may comprise from about 0.1% to about 10%, and in some examples, from about 0.1% to about 8%, and in other examples, from about 0.1% to about 6%, by weight of the detergent composition, of alkoxylated polyamines.

Carboxylate polymer—The detergent composition may also include one or more carboxylate polymers, which may optionally be sulfonated. Suitable carboxylate polymers include a maleate/acrylate random copolymer or a poly(meth)acrylate homopolymer. In one aspect, the carboxylate polymer is a poly(meth)acrylate homopolymer having a molecular weight from 4,000 Da to 9,000 Da, or from 6,000 Da to 9,000 Da.

Alkoxylated polycarboxylates may also be used in the detergent compositions herein to provide grease removal. Such materials are described in WO 91/08281 and PCT 90/01815. Chemically, these materials comprise poly(meth)acrylates having one ethoxy side-chain per every 7-8 (meth)acrylate units. The side-chains are of the formula —($CH_2CH_2O$)$_m$ ($CH_2$)$_n$$CH_3$ wherein m is 2-3 and n is 6-12. The side-chains are ester-linked to the polyacrylate "backbone" to provide a "comb" polymer type structure. The molecular weight can vary, but may be in the range of about 2000 to about 50,000. The detergent compositions described herein may comprise from about 0.1% to about 10%, and in some examples, from about 0.25% to about 5%, and in other examples, from about 0.3% to about 2%, by weight of the detergent composition, of alkoxylated polycarboxylates.

The compositions may include an amphiphilic graft co-polymer. A suitable amphiphilic graft co-polymer comprises (i) a polyethyelene glycol backbone; and (ii) and at least one pendant moiety selected from polyvinyl acetate, polyvinyl alcohol and mixtures thereof. A suitable amphilic graft co-polymer is Sokalan® HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is typically about 6000 and the weight ratio of the polyethylene oxide to polyvinyl acetate is about 40 to 60 and no more than 1 grafting point per 50 ethylene oxide units.

Soil Release Polymer

The detergent compositions of the present invention may also include one or more soil release polymers having a structure as defined by one of the following structures (I), (II) or (III):

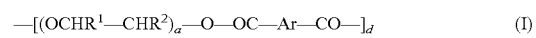

—[(OCHR$^1$—CHR$^2$)$_a$—O—OC—Ar—CO—]$_d$ (I)

—[(OCHR$^3$—CHR$^4$)$_b$—O—OC-sAr—CO—]$_e$ (II)

—[(OCHR$^5$—CHR$^6$)$_c$—OR$^7$]$_f$ (III)

wherein:
a, b and c are from 1 to 200;
d, e and f are from 1 to 50;
Ar is a 1,4-substituted phenylene;
sAr is 1,3-substituted phenylene substituted in position 5 with SO$_3$Me;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
R$^1$, R$^2$, R$^3$, R$^4$, R$^5$ and R$^6$ are independently selected from H or $C_1$-$C_{18}$n- or iso-alkyl; and
R$^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clamant. Other suitable soil release polymers are Marloquest polymers, such as Marloquest SL supplied by Sasol.

Cellulosic Polymer

The cleaning compositions of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixures thereof. In one aspect, the carboxymethyl cellulose has a degree of carboxymethyl substitution from 0.5 to 0.9 and a molecular weight from 100,000 Da to 300,000 Da.

Amines

Amines may be used in the compositions described herein for added removal of grease and particulates from soiled materials. The compositions described herein may comprise from about 0.1% to about 10%, in some examples, from about 0.1% to about 4%, and in other examples, from about 0.1% to about 2%, by weight of the detergent composition, of additional amines. Non-limiting examples of additional amines may include, but are not limited to, polyetheramines, polyamines, oligoamines, triamines, diamines, pentamines, tetraamines, or combinations thereof. Specific examples of suitable additional amines include tetraethylenepentamine, triethylenetetraamine, diethylenetriamine, or a mixture thereof.

Bleaching Agents

The detergent compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the detergent compositions of the present invention may comprise from about 0.1% to about 50% or even from about 0.1% to about 25% bleaching agent by weight of the detergent composition.

Bleach Catalysts

The detergent compositions of the present invention may also include one or more bleach catalysts capable of accepting an oxygen atom from a peroxyacid and/or salt thereof, and transferring the oxygen atom to an oxidizeable substrate. Suitable bleach catalysts include, but are not limited to: minimum cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Brighteners

Optical brighteners or other brightening or whitening agents may be incorporated at levels of from about 0.01% to about 1.2%, by weight of the composition, into the detergent compositions described herein. Commercial fluorescent brighteners suitable for the present invention can be classified into subgroups, including but not limited to: derivatives of stilbene, pyrazoline, coumarin, benzoxazoles, carboxylic acid, methinecyanines, dibenzothiophene-5,5-dioxide, azoles, 5- and 6-membered-ring heterocycles, and other miscellaneous agents.

In some examples, the fluorescent brightener is selected from the group consisting of disodium 4,4'-bis{[4-anilino-6-morpholino-s-triazin-2-yl]-amino}-2,2'-stilbenedisulfonate (brightener 15, commercially available under the tradename Tinopal AMS-GX by Ciba Geigy Corporation), disodium4,4'-bis{[4-anilino-6-(N-2-bis-hydroxyethyl)-s-triazine-2-yl]-amino}-2,2'-stilbenedisulonate (commercially available under the tradename Tinopal UNPA-GX by Ciba-Geigy Corporation), disodium 4,4'-bis{[4-anilino-6-(N-2-hydroxyethyl-N-methylamino)-s-triazine-2-yl]-amino}-2, 2'-stilbenedisulfonate (commercially available under the tradename Tinopal 5BM-GX by Ciba-Geigy Corporation). More preferably, the fluorescent brightener is disodium 4,4'-bis{[4-anilino-6-morpholino-s-triazin-2-yl]-amino}-2, 2'-stilbenedisulfonate.

The brighteners may be added in particulate form or as a premix with a suitable solvent, for example nonionic surfactant, propanediol.

Fabric Hueing Agents

The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes also include small molecule dyes and polymeric dyes. Suitable small molecule dyes include small molecule dyes selected from the group consisting of dyes falling into the Colour Index (C.I.) classifications of Direct, Basic, Reactive or hydrolysed Reactive, Solvent or Disperse dyes for example that are classified as Blue, Violet, Red, Green or Black, and provide the desired shade either alone or in combination. Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Suitable polymeric dyes also include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. Suitable polymeric dyes also include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

The aforementioned fabric hueing agents can be used in combination (any mixture of fabric hueing agents can be used).

Encapsulates

The compositions may comprise an encapsulate. The encapsulate may comprise a core, a shell having an inner and outer surface, where the shell encapsulates the core.

The encapsulate may comprise a core and a shell, where the core comprises a material selected from perfumes; brighteners; dyes; insect repellants; silicones; waxes; flavors; vitamins; fabric softening agents; skin care agents, e.g., paraffins; enzymes; anti-bacterial agents; bleaches; sensates; or mixtures thereof; and where the shell comprises a material selected from polyethylenes; polyamides; polyvinylalcohols, optionally containing other co-monomers; polystyrenes; polyisoprenes; polycarbonates; polyesters; polyacrylates; polyolefins; polysaccharides, e.g., alginate and/or chitosan; gelatin; shellac; epoxy resins; vinyl polymers; water insoluble inorganics; silicone; aminoplasts, or mixtures thereof. When the shell comprises an aminoplast, the aminoplast may comprise polyurea, polyurethane, and/or polyureaurethane. The polyurea may comprise polyoxymethyleneurea and/or melamine formaldehyde.

The encapsulate may comprise a core, and the core may comprise a perfume. The encapsulate may comprise a shell, and the shell may comprise melamine formaldehyde and/or cross linked melamine formaldehyde. The encapsulate may comprise a core comprising a perfume and a shell comprising melamine formaldehyde and/or cross linked melamine formaldehyde Suitable encapsulates may comprise a core material and a shell, where the shell at least partially surrounds the core material. The core of the encapsulate comprises a material selected from a perfume raw material and/or optionally another material, e.g., vegetable oil, esters of vegetable oils, esters, straight or branched chain hydrocarbons, partially hydrogenated terphenyls, dialkyl phthalates, alkyl biphenyls, alkylated naphthalene, petroleum spirits, aromatic solvents, silicone oils, or mixtures thereof.

The wall of the encapsulate may comprise a suitable resin, such as the reaction product of an aldehyde and an amine. Suitable aldehydes include formaldehyde. Suitable amines include melamine, urea, benzoguanamine, glycoluril, or mixtures thereof. Suitable melamines include methylol melamine, methylated methylol melamine, imino melamine and mixtures thereof. Suitable ureas include, dimethylol urea, methylated dimethylol urea, urea-resorcinol, or mixtures thereof.

Suitable formaldehyde scavengers may be employed with the encapsulates, for example, in a capsule slurry and/or added to a composition before, during, or after the encapsulates are added to such composition.

Suitable capsules can be purchased from Appleton Papers Inc. of Appleton, Wis. USA.

Perfumes

Perfumes and perfumery ingredients may be used in the detergent compositions described herein. Non-limiting examples of perfume and perfumery ingredients include, but are not limited to, aldehydes, ketones, esters, and the like. Other examples include various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes may be included at a concentration ranging from about 0.01% to about 2% by weight of the detergent composition.

Dye Transfer Inhibiting Agents

Fabric detergent compositions may also include one or more materials effective for inhibiting the transfer of dyes from one fabric to another during the cleaning process. Generally, such dye transfer inhibiting agents may include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents may be used at a concentration of about 0.0001% to about 10%, by weight of the composition, in some examples, from about 0.01% to about 5%, by weight of the composition, and in other examples, from about 0.05% to about 2% by weight of the composition.

Chelating Agents

The detergent compositions described herein may also contain one or more metal ion chelating agents. Suitable molecules include copper, iron and/or manganese chelating agents and mixtures thereof. Such chelating agents can be selected from the group consisting of phosphonates, amino carboxylates, amino phosphonates, succinates, polyfunctionally-substituted aromatic chelating agents, 2-pyridinol-N-oxide compounds, hydroxamic acids, carboxymethyl inulins and mixtures thereof. Chelating agents can be present in the acid or salt form including alkali metal, ammonium, and substituted ammonium salts thereof, and mixtures thereof. Other suitable chelating agents for use herein are the commercial DEQUEST series, and chelants from Monsanto, Akzo-Nobel, DuPont, Dow, the Trilon® series from BASF and Nalco.

The chelant may be present in the detergent compositions disclosed herein at from about 0.005% to about 15% by weight, about 0.01% to about 5% by weight, about 0.1% to about 3.0% by weight, or from about 0.2% to about 0.7% by weight, or from about 0.3% to about 0.6% by weight of the detergent compositions disclosed herein.

Suds Suppressors

Compounds for reducing or suppressing the formation of suds can be incorporated into the detergent compositions described herein. Suds suppression can be of particular importance in the so-called "high concentration cleaning process" and in front-loading style washing machines. The detergent compositions herein may comprise from 0.1% to about 10%, by weight of the composition, of suds suppressor.

Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols.

Additional suitable antifoams are those derived from phenylpropylmethyl substituted polysiloxanes.

The detergent composition may comprise a suds suppressor selected from organomodified silicone polymers with aryl or alkylaryl substituents combined with silicone resin and a primary filler, which is modified silica. The detergent compositions may comprise from about 0.001% to about 4.0%, by weight of the composition, of such a suds suppressor.

The detergent composition comprises a suds suppressor selected from: a) mixtures of from about 80 to about 92% ethylmethyl, methyl(2-phenylpropyl) siloxane; from about 5 to about 14% MQ resin in octyl stearate; and from about 3 to about 7% modified silica; b) mixtures of from about 78 to about 92% ethylmethyl, methyl(2-phenylpropyl) siloxane; from about 3 to about 10% MQ resin in octyl stearate; from about 4 to about 12% modified silica; or c) mixtures thereof, where the percentages are by weight of the anti-foam.

Suds Boosters

If high sudsing is desired, suds boosters such as the $C_{10}$-$C_{16}$ alkanolamides may be incorporated into the detergent compositions at a concentration ranging from about 1% to about 10% by weight of the detergent composition. Some examples include the $C_{10}$-$C_{14}$ monoethanol and diethanol amides. If desired, water-soluble magnesium and/or calcium salts such as $MgCl_2$, $MgSO_4$, $CaCl_2$, $CaSO_4$, and the like, may be added at levels of about 0.1% to about 2% by weight of the detergent composition, to provide additional suds and to enhance grease removal performance.

Conditioning Agents

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. The high melting point fatty compound is included in the composition at a level of from about 0.1% to about 40%, preferably from about 1% to about 30%, more preferably from about 1.5% to about 16% by weight of the composition, from about 1.5% to about 8%.

The composition of the present invention may include a nonionic polymer as a conditioning agent.

Suitable conditioning agents for use in the composition include those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. The concentration of the silicone conditioning agent typically ranges from about 0.01% to about 10%.

The compositions of the present invention may also comprise from about 0.05% to about 3% of at least one organic conditioning oil as the conditioning agent, either alone or in combination with other conditioning agents, such as the silicones (described herein). Suitable conditioning oils include hydrocarbon oils, polyolefins, and fatty esters.

Fabric Enhancement Polymers

Suitable fabric enhancement polymers are typically cationically charged and/or have a high molecular weight. Suitable concentrations of this component are in the range from 0.01% to 50%, preferably from 0.1% to 15%, more preferably from 0.2% to 5.0%, and most preferably from 0.5% to 3.0% by weight of the composition. The fabric enhancement polymers may be a homopolymer or be formed from two or more types of monomers. The monomer weight of the polymer will generally be between 5,000 and 10,000,000, typically at least 10,000 and preferably in the range 100,000 to 2,000,000. Preferred fabric enhancement polymers will have cationic charge densities of at least 0.2 meq/gm, preferably at least 0.25 meq/gm, more preferably at least 0.3 meq/gm, but also preferably less than 5 meq/gm, more preferably less than 3 meq/gm, and most preferably less than 2 meq/gm at the pH of intended use of the composition, which pH will generally range from pH 3 to pH 9, preferably between pH 4 and pH 8. The fabric enhancement polymers may be of natural or synthetic origin.

Pearlescent Agent

The laundry detergent compositions of the invention may comprise a pearlescent agent. Non-limiting examples of pearlescent agents include: mica; titanium dioxide coated mica; bismuth oxychloride; fish scales; mono and diesters of alkylene glycol. The pearlescent agent may be ethyleneglycoldistearate (EGDS).

Hygiene and Malodour

The compositions of the present invention may also comprise one or more of zinc ricinoleate, thymol, quaternary ammonium salts such as Bardac®, polyethylenimines (such as Lupasol® from BASF) and zinc complexes thereof, silver and silver compounds, especially those designed to slowly release $Ag^+$ or nano-silver dispersions.

Buffer System

The detergent compositions described herein may be formulated such that, during use in aqueous cleaning operations, the wash water will have a pH of between about 7.0 and about 12, and in some examples, between about 7.0 and about 11. Techniques for controlling pH at recommended usage levels include the use of buffers, alkalis, or acids, and are well known to those skilled in the art. These include, but are not limited to, the use of sodium carbonate, citric acid or sodium citrate, lactic acid or lactate, monoethanol amine or other amines, boric acid or borates, and other pH-adjusting compounds well known in the art.

The detergent compositions herein may comprise dynamic in-wash pH profiles. Such detergent compositions may use wax-covered citric acid particles in conjunction with other pH control agents such that (i) about 3 minutes after contact with water, the pH of the wash liquor is greater than 10; (ii) about 10 minutes after contact with water, the pH of the wash liquor is less than 9.5; (iii) about 20 minutes after contact with water, the pH of the wash liquor is less than 9.0; and (iv) optionally, wherein, the equilibrium pH of the wash liquor is in the range of from about 7.0 to about 8.5.

Water-Soluble Film

The compositions of the present disclosure may be encapsulated within a water-soluble film, for example, a film comprising polyvinyl alcohol (PVOH).

Other Adjunct Ingredients

A wide variety of other ingredients may be used in the detergent compositions herein, including other active ingredients, carriers, hydrotropes, processing aids, dyes or pigments, solvents for liquid formulations, and solid or other liquid fillers, erythrosine, colliodal silica, waxes, probiotics, surfactin, aminocellulosic polymers, Zinc Ricinoleate, perfume microcapsules, rhamnolipids, sophorolipids, glycopeptides, methyl ester sulfonates, methyl ester ethoxylates, sulfonated estolides, cleavable surfactants, biopolymers, silicones, modified silicones, aminosilicones, deposition aids, locust bean gum, cationic hydroxyethylcellulose polymers, cationic guars, hydrotropes (especially cumenesulfonate salts, toluenesulfonate salts, xylenesulfonate salts, and naphalene salts), antioxidants, BHT, PVA particle-encapsulated dyes or perfumes, pearlescent agents, effervescent agents, color change systems, silicone polyurethanes, opacifiers, tablet disintegrants, biomass fillers, fast-dry silicones, glycol distearate, hydroxyethylcellulose polymers, hydrophobically modified cellulose polymers or hydroxyethylcellulose polymers, starch perfume encapsulates, emulsified oils, bisphenol antioxidants, microfibrous cellulose structurants, properfumes, styrene/acrylate polymers, triazines, soaps, superoxide dismutase, benzophenone protease inhibitors, functionalized TiO2, dibutyl phosphate, silica perfume capsules, and other adjunct ingredients, silicate salts (e.g., sodium silicate, potassium silicate), choline oxidase, pectate lyase, mica, titanium dioxide coated mica, bismuth oxychloride, and other actives.

The compositions described herein may also contain vitamins and amino acids such as: water soluble vitamins and their derivatives, water soluble amino acids and their salts and/or derivatives, water insoluble amino acids viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, vitamins, niacinamide, caffeine, and minoxidil.

The compositions of the present invention may also contain pigment materials such as nitroso, monoazo, disazo, carotenoid, triphenyl methane, triaryl methane, xanthene, quinoline, oxazine, azine, anthraquinone, indigoid, thionindigoid, quinacridone, phthalocianine, botanical, and natural colors, including water soluble components such as those having C.I. Names. The detergent compositions of the present invention may also contain antimicrobial agents.

Water

The compositions disclosed herein may comprise from about 1% to about 80%, by weight of the composition, water. When the composition is a heavy duty liquid detergent composition, the composition typically comprises from about 40% to about 80% water. When the composition is a compact liquid detergent, the composition typically comprises from about 20% to about 60%, or from about 30% to about 50% water. When the composition is in unit dose form, for example, encapsulated in water-soluble film, the composition typically comprises less than 20%, or less than 15%, or less than 12%, or less than 10%, or less than 8%, or less than 5% water. The composition may comprise from about 1% to 20%, or from about 3% to about 15%, or from about 5% to about 12%, by weight of the composition, water. When the composition is in unitized dose form, for example, encapsulated in water-soluble film, the composition typically comprises less than 20%, or less than 15%, or less than 12%, or less than 10%, or less than 8%, or less than 5% water. The composition may comprise from about 1% to 20%, or from about 3% to about 15%, or from about 5% to about 12%, by weight of the composition, water.

Composition Form

The compositions disclosed herein may be a form selected from the group consisting of a liquid laundry detergent, a gel detergent, a single-phase or multi-phase unit dose detergent, a detergent contained in a single-phase or multi-phase or multi-compartment water soluble pouch, a liquid hand dishwashing composition, a laundry pretreat product, a fabric softener composition, and mixtures thereof.

Methods of Use

The present invention includes methods for cleaning soiled material. Compact fluid detergent compositions that are suitable for sale to consumers are suited for use in laundry pretreatment applications, laundry cleaning applications, and home care applications.

Such methods include, but are not limited to, the steps of contacting detergent compositions in neat form or diluted in wash liquor, with at least a portion of a soiled material and then optionally rinsing the soiled material. The soiled material may be subjected to a washing step prior to the optional rinsing step.

For use in laundry pretreatment applications, the method may include contacting the detergent compositions described herein with soiled fabric. Following pretreatment, the soiled fabric may be laundered in a washing machine or otherwise rinsed.

Machine laundry methods may comprise treating soiled laundry with an aqueous wash solution in a washing machine having dissolved or dispensed therein an effective amount of a machine laundry detergent composition in accord with the invention. An "effective amount" of the detergent composition means from about 20 g to about 300 g of product dissolved or dispersed in a wash solution of volume from about 5L to about 65L. The water temperatures may range from about 5° C. to about 100° C. The water to soiled material (e.g., fabric) ratio may be from about 1:1 to about 30:1. The compositions may be employed at concentrations of from about 500 ppm to about 15,000 ppm in solution. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The detergent compositions herein may be used for laundering of fabrics at reduced wash temperatures. These methods of laundering fabric comprise the steps of delivering a laundry detergent composition to water to form a wash liquor and adding a laundering fabric to said wash liquor, wherein the wash liquor has a temperature of from about 0° C. to about 20° C., or from about 0° C. to about 15° C., or from about 0° C. to about 9° C. The fabric may be contacted to the water prior to, or after, or simultaneous with, contacting the laundry detergent composition with water.

Another method includes contacting a nonwoven substrate, which is impregnated with the detergent composition, with a soiled material. As used herein, "nonwoven substrate" can comprise any conventionally fashioned nonwoven sheet or web having suitable basis weight, caliper (thickness), absorbency, and strength characteristics. Non-limiting examples of suitable commercially available nonwoven substrates include those marketed under the tradenames SONTARA® by DuPont and POLYWEB® by James River Corp.

Hand washing/soak methods, and combined handwashing with semi-automatic washing machines, are also included.

Packaging for the Compositions

The compact fluid detergent compositions that are suitable for consumer use can be packaged in any suitable container including those constructed from paper, cardboard, plastic materials, and any suitable laminates. The compact fluid detergent compositions may also be encapsulated in water-soluble film and packaged as a unitized dose detergent composition, for example, mono-compartment pouches or multi-compartment pouches having superposed and/or side-by-side compartments.

Specific contemplated aspects of the disclosure are herein described in the following numbered paragraphs.

1. A compound of formula (I)

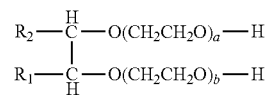

wherein each of $R_1$ and $R_2$ is independently selected from a substituted or unsubstituted, linear or branched, saturated or unsaturated $C_1$-$C_6$ alkyl group, preferably a substituted or unsubstituted, linear or branched, saturated or unsaturated $C_1$-$C_3$ alkyl group, more preferably a $C_1$ alkyl group and a+b has an average value of greater than 0, or greater than or equal to 0.1, or greater than or equal to 0.5, or greater than or equal to 1 and less than or equal to about 20, or less than or equal to about 15, or less than or equal to about 10, preferably a+b has an average value of greater than 0 and less than or equal to about 20.

2. A composition comprising from about 10% to about 50% by weight of a surfactant, a solvent comprising an ethoxylated diol of formula (I)

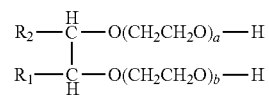

wherein each of $R_1$ and $R_2$ is independently selected from a substituted or unsubstituted, linear or branched, saturated or unsaturated $C_1$-$C_6$ alkyl group, preferably a substituted or unsubstituted, linear or branched, saturated or unsaturated $C_1$-$C_3$ alkyl group, more preferably a $C_1$ alkyl group and a+b has an average value of greater than 0, or greater than or equal to 0.1, or greater than or equal to 0.5, or greater than or equal to 1 and less than or equal to about 20, or less than or equal to about 15, or less than or equal to about 10, preferably a+b has an average value of greater than 0 and less than or equal to about 20, an adjunct, and water.

3. A composition comprising, consisting essentially of, or consisting of from about 30% to about 75% by weight of an anionic surfactant, a solvent comprising an ethoxylated diol of formula (I)

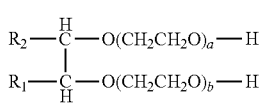

wherein each of $R_1$ and $R_2$ is independently selected from a substituted or unsubstituted, linear or branched, saturated or unsaturated $C_1$-$C_6$ alkyl group, preferably a substituted or unsubstituted, linear or branched, saturated or unsaturated $C_1$-$C_3$ alkyl group, more preferably a $C_1$ alkyl group and a+b has an average value of greater than 0, or greater than or equal to 0.1, or greater than or equal to 0.5, or greater than or equal to 1 and less than or equal to about 20, or less than or equal to about 15, or less than or equal to about 10, preferably a+b has an average value of greater than 0 and less than or equal to about 20, and water.

4. The composition of any of the preceding paragraphs wherein said solvent further comprises a monoalcohol of formula (II)

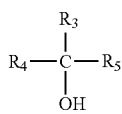

wherein each of $R_3$, $R_4$, and $R_5$ is independently selected from H or a substituted or unsubstituted, linear or branched $C_1$-$C_6$ alkyl group, glycerine, propoxylated glycerine, ethoxylated glycerine, propylene glycol, diethylene glycol, dipropylene glycol, or mixtures thereof.

5. The composition of paragraph 2 wherein the surfactant is selected from the group consisting of anionic surfactant, cationic surfactant, nonionic surfactant, amphoteric surfactant, zwitterionic surfactant, and mixtures thereof.

6. The composition of paragraph 5 wherein said anionic surfactant is selected from the group consisting of linear or branched alkyl benzene sulfonates, linear or branched alkoxylated alkyl sulfates, linear or branched alkyl sulfates, methyl ester sulfonates, paraffin sulfonates, α-olefin sulfonates, internal olefin sulfonates, and mixtures thereof.

7. The composition of paragraph 3 wherein said anionic surfactant is selected from the group consisting of linear or branched alkyl benzene sulfonates, linear or branched alkoxylated alkyl sulfates, linear or branched alkyl sulfates, and mixtures thereof.

8. The composition of paragraph 3 wherein said anionic surfactant is a linear or branched alkoxylated alkyl sulfate.

9. The composition of paragraph 3 wherein said anionic surfactant is a 2-alkyl branched primary alkyl sulfate.

10. The composition of any of the preceding paragraphs wherein said composition comprises less than about 20% water.

11. The composition of paragraph 2 wherein said adjunct is selected from the group consisting of a structurant, a builder, an organic polymeric compound, an enzyme, an enzyme stabilizer, a bleach system, a brightener, a hueing agent, a chelating agent, a suds suppressor, a conditioning agent, a humectant, a perfume, a perfume microcapsule, a filler or carrier, an alkalinity system, a pH control system, a buffer, an alkanolamine, and mixtures thereof.

12. The composition of paragraph 11 wherein said enzyme is selected from the group consisting of lipase, amylase, protease, mannanase, cellulase, pectinase, and mixtures thereof.

13. The composition of paragraph 11 wherein said composition comprises from about 0.001% to about 1% by weight of enzyme.

14. The composition of paragraph 2 wherein said composition is a form selected from the group consisting of a liquid laundry detergent, a gel detergent, a single-phase or multi-phase unit dose detergent, a detergent contained in a single-phase or multi-phase or multi-compartment water-soluble pouch, a liquid hand dishwashing composition, a laundry pretreat product, a fabric softener composition, and mixtures thereof.

15. The composition of paragraph 14 wherein said composition is a detergent contained in a single-phase or multi-phase or multi-compartment water-soluble pouch.

16. A process for manufacturing an aqueous liquid or gel-form laundry detergent comprising the steps of:
(i) at a first location, preparing a shippable anionic surfactant paste comprising, consisting essentially of, or consisting of:
from about 30% to about 75% by weight of anionic surfactant,
from about 3% to about 18% by weight of a solvent comprising an ethoxylated diol of formula (I)

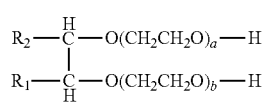

wherein each of $R_1$ and $R_2$ is independently selected from a substituted or unsubstituted, linear or branched, saturated or unsaturated $C_1$-$C_6$ alkyl group, and a+b has an average value of greater than 0 and less than or equal to about 20, and water;
(ii) shipping the anionic surfactant paste to a second location;
(iii) at the second location, adding said anionic surfactant paste to a composition comprising a surfactant and adjuncts.

17. The process of paragraph 16 wherein said anionic surfactant is $C_{12}$-$C_{16}$ linear or branched alkoxylated alkyl sulfate, preferably $C_{14}$-$C_{16}$ linear or branched alkoxylated alkyl sulfate.

18. The process of paragraph 16 wherein said anionic surfactant is selected from the group consisting of 2-alkyl branched primary alkyl sulfates.

EXAMPLES

Example 1

Synthesis of Ethoxylated 2,3-butanediol

Reaction:

2,3-butanediol (2,3-BDO) is added to a reactor along with a catalyst (0.5 mole % potassium, as a 25% potassium methoxide in methanol solution). The reactor is purged of air using a vacuum and nitrogen cycles. Volatile materials (methanol and water) are removed by sparging with nitrogen and vacuum at 110° C.-115° C. (sparging is done by slowly adding a trickle of nitrogen through the bottom drain valve, while using a water aspirator vacuum). After 1-2 hours, the reactor is filled with nitrogen and vented to 0-5 psig and then heated to between 110° C. and 125° C. Ethylene oxide is slowly added while stirring at 400 rpm (used throughout) and maintaining the pressure below 200 psig. Each step of the reaction is allowed to run until the pressure decreases, levels off, and is constant for at least 30 minutes.

The addition of ethylene oxide continues until the desired degree of ethoxylation is attained, as measured by increase in weight. The product formed is understood to have an average degree of ethoxylation and represents a mixture of ethoxylate 2,3-BDO compounds. For example, 1 mole of 2,3-BDO with one mole of EO added is represented by 2,3-BDO EO1. Samples having a degree of ethoxylation ranging from 3 to 7, as measured by the moles of 2,3-BDO to moles of ethylene oxide added, are prepared.

Prior to collecting samples, residual ethylene oxide is removed by sparging with nitrogen and a vacuum at 110° C. The reactor is then cooled to below 80° C. and the sample is drained from the reactor, while keeping the container purged with nitrogen. After cooling, the sample is neutralized using acetic acid and blanketed with nitrogen.

The reactor used is a Model Number 4572 Parr 1800 ml reactor constructed of T316 stainless steel. It has a magnetic drive stirring assembly that uses an electric motor for agitation. The stir shaft has 2-inch pitched blade impellers. The reactor has a cooling coil and water is used in the cooling coil to keep the temperature from exceeding a programmed set-point. The reactor is monitored and controlled by a Camile data acquisition and control system.

Surfactant Paste and Detergent Samples

Test samples are prepared by standard methods of mixing in a container and, if necessary, are neutralized to pH above 7 and less than 9 for sufficient stability of sulfated surfactants. Sample size is sufficient for accurate weighing of components. Reference samples are matched to samples containing the solvents disclosed herein and placed in a controlled temperature storage room of either 40° C. or 20° C. for periods ranging from 1 week to 4 weeks with periodic visual assessment of the physical state of the sample.

Analysis

Samples are visually evaluated as either passing or failing. Passing samples are visually clear, homogeneous, with no substantial haze or precipitate, and free flowing, when the container is inverted. Failing samples are substantially hazy, have more than one phase (e.g., two distinct visible layers), contain some visible precipitate, or form a gel (semi-solid single layer) that does not flow upon inversion of the container. For example, samples that are free flowing but have more than one phase are evaluated as failing.

The results below in Examples 2-3 are visually evaluated as passing or failing, based on the criteria discussed above.

Example 2

Compositions Containing 37% Sodium 2-alkylbranched Alcohol Sulfate

Comparison of ethoxylated 2,3-butanediol (e.g., 2,3-BDO EO3) solvents versus 1,2-propylene glycol (PG), measured as percent reduction over 1,2-propylene glycol (PG), with water added as balance of components.

TABLE 1

| Solvent Ingredient: | % solvent level reduction over PG |
|---|---|
| 2,3-BDO | 20% |
| 2,3-BDO EO3 | 40% |
| 2,3-BDO EO5 | 57% |
| 2,3-BDO EO7 | 57% |

Example 3

Compositions Containing Sodium Alkyl Ethoxy Sulfate (AES)

Comparison of ethoxylated 2,3-butanediol (e.g., 2,3-BDO EO3) solvents versus 1,2-propylene glycol (PG) solvent, measured as percent reduction over 1,2-propylene Glycol (PG).

The compositions each contain 53% AES, 7.6% ethanol, and water added as balance of components.

TABLE 2

| Solvent Ingredient: | % solvent level reduction over PG |
|---|---|
| 2,3-BDO | 20% |
| 2,3-BDO EO3 | 40% |
| 2,3-BDO EO5 | 20% |
| 2,3-BDO EO7 | 20% |

Detergent Formulation Examples

Example 4

Heavy Duty Liquid Laundry Detergent Compositions

TABLE 3

|  | (wt %) | (wt %) | (wt %) | (wt %) | (wt %) | (wt %) |
|---|---|---|---|---|---|---|
| Ethoxylated Diol | 1.5 | 3 | 2 | 8 | 3 | 3 |
| Ethanol | 1.1 | 2 | 1 | 0 | 2 | 2 |
| Diethylene glycol | 0 | 3 | 0 | 0 | 0 | 0 |
| 1,2-Propanediol | 1.7 | 0 | 1 | 0 | 3 | 3 |
| Dipropylene glycol | 0 | 0 | 0 | 0 | 0 | 0 |
| Glycerine | 0 | 0 | 0 | 0.1 | 0 | 0.1 |
| Sodium cumene sulphonate | 0 | 0 | 0 | 2 | 0 | 1 |
| MES | 0 | 0 | 0 | 0 | 4 | 0 |
| AES | 9 | 17 | 3 | 2 | 1 | 15 |
| LAS | 1.5 | 7 | 15 | 6 | 4 | 4 |
| HSAS | 0 | 3 | 0 | 0 | 0 | 0 |
| Isalchem ® 156 | 0 | 0 | 0 | 12 | 0 | 0 |
| AE | 0 | 0.6 | 3 | 4 | 1 | 6 |

TABLE 3-continued

|  | (wt %) | (wt %) | (wt %) | (wt %) | (wt %) | (wt %) |
|---|---|---|---|---|---|---|
| Lauryl Trimethyl Ammonium Chloride | 0 | 1 | 0.5 | 0.25 | 0 | 0 |
| $C_{12-14}$ dimethyl Amine Oxide | 0.3 | 2 | 0.23 | 0 | 0 | 0 |
| Sodium formate | 1.6 | 0.09 | 1.2 | 1.6 | 0 | 0.2 |
| Calcium formate | 0 | 0 | 0 | 0 | 0.13 | 0 |
| Calcium Chloride | 0.01 | 0.08 | 0 | 0 | 0 | 0 |
| Monoethanolamine | 1.4 | 1.0 | 4.0 | 0 | 0 | To pH 8.2 |
| Diethylene glycol | 5.5 | 0.0 | 4.1 | 0.7 | 0 | 0 |
| Chelant | 0.15 | 0.15 | 0.11 | 0.5 | 0.11 | 0.8 |
| Citric Acid | 2.5 | 3.96 | 1.88 | 0.9 | 2.5 | 0.6 |
| $C_{12-18}$ Fatty Acid | 0.8 | 3.5 | 0.6 | 1.2 | 0 | 15.0 |
| 4-formyl-phenylboronic acid | 0 | 0 | 0 | 0.1 | 0.02 | 0.01 |
| Borax | 1.43 | 2.1 | 1.1 | 0 | 1.07 | 0 |
| Ethoxylated Polyethylenimine | 0 | 1.4 | 0 | 0 | 0 | 0.8 |
| Zwitterionic ethoxylated quaternized sulfated hexamethylene diamine | 2.1 | 0 | 0.7 | 0.3 | 1.6 | 0 |
| PEG-PVAc Polymer | 0.1 | 0.2 | 0.0 | 0.05 | 0.0 | 1 |
| Grease Cleaning Alkoxylated Polyalkylenimine Polymer | 1 | 2 | 0 | 1.5 | 0 | 0 |
| Fluorescent Brightener | 0.2 | 0.1 | 0.05 | 0.15 | 0.3 | 0.2 |
| Hydrogenated castor oil derivative structurant | 0.1 | 0 | 0.4 | 0 | 0 | 0.1 |
| Perfume | 1.6 | 1.1 | 1.0 | 0.9 | 1.5 | 1.6 |
| Core Shell Melamine-formaldehyde encapsulate of perfume | 0.5 | 0.05 | 0.00 | 0.1 | 0.05 | 0.1 |
| Protease (40.6 mg active/g) | 0.8 | 0.6 | 0.7 | 0.7 | 0.2 | 1.5 |
| Mannanase: Mannaway ® (25 mg active/g) | 0.07 | 0.05 | 0 | 0.04 | 0.045 | 0.1 |
| Amylase: Stainzyme ® (15 mg active/g) | 0.3 | 0 | 0.3 | 0 | 0.6 | 0.1 |
| Amylase: Natalase ® (29 mg active/g) | 0 | 0.6 | 0.1 | 0.07 | 0 | 0.1 |
| Xyloglucanase (Whitezyme ®, 20 mg active/g) | 0.2 | 0.1 | 0 | 0.05 | 0.05 | 0.2 |
| Lipex ® (18 mg active/g) | 0.4 | 0.2 | 0.3 | 0.2 | 0 | 0 |
| *Water, dyes & minors |  |  | Balance |  |  |  |

*Based on total cleaning and/or treatment composition weight
All enzyme levels are expressed as % enzyme raw material.

Example 5

Unit Dose Compositions—Unit Dose Laundry Detergent Formulations can Comprise One or Multiple Compartments

TABLE 4

| Ingredient | (wt %) | (wt %) | (wt %) | wt %) | (wt %) |
|---|---|---|---|---|---|
| Ethoxylated diol | 4 | 5 | 3 | 4 | 2 |
| 1,2 propanediol | 7 | 13.8 | 13.8 | 13.8 | 13.8 |
| Glycerine | 4 | 0 | 3.1 | 2.1 | 4.1 |
| Dipropylene Glycol | 4 | 0 | 0 | 0 | 0 |
| Sodium cumene sulphonate | 0 | 0 | 0 | 0 | 2.0 |
| AES | 8 | 18 | 9.5 | 12.5 | 10 |
| LAS | 5 | 18 | 9.5 | 14.5 | 7.5 |
| Isalchem ® 156 | 15 | 0 | 5 | 0 | 10 |
| AE | 13 | 3 | 16 | 2 | 13 |
| Citric Acid | 1 | 0.6 | 0.6 | 1.56 | 0.6 |
| $C_{12-18}$ Fatty Acid | 4.5 | 10 | 4.5 | 14.8 | 4.5 |
| Enzymes | 1.0 | 1.7 | 1.7 | 2.0 | 1.7 |
| Ethoxylated Polyethylenimine | 1.4 | 1.4 | 4.0 | 6.0 | 4.0 |
| Chelant | 0.6 | 0.6 | 1.2 | 1.2 | 3.0 |
| PEG-PVAc Polymer | 4 | 2.5 | 4 | 2.5 | 1.5 |
| Fluorescent Brightener | 0.15 | 0.4 | 0.3 | 0.3 | 0.3 |
| Monoethanolamine | 9.8 | 8.0 | 8.0 | 8.0 | 9.8 |
| TIPA | 0 | 0 | 2.0 | 0 | 0 |
| Triethanolamine | 0 | 2.0 | 0 | 0 | 0 |

TABLE 4-continued

| Ingredient | (wt %) | (wt %) | (wt %) | wt %) | (wt %) |
|---|---|---|---|---|---|
| Cyclohexyl dimethanol | 0 | 0 | 0 | 2.0 | 0 |
| Water | 12 | 10 | 10 | 10 | 10 |
| Structurant | 0.1 | 0.14 | 0.14 | 0.1 | 0.14 |
| Perfume | 0.2 | 1.9 | 1 | 1.9 | 1.9 |
| Hueing Agent | 0 | 0.1 | 0.001 | 0.0001 | 0 |
| Buffers |  |  | To pH 8.0 |  |  |
| Other Solvents (ethanol) |  |  | To 100% |  |  |

All enzyme levels are expressed as % enzyme raw material.

Raw Materials for Examples 4-5

LAS is linear alkylbenzenesulfonate having an average aliphatic carbon chain length $C_{11}$-$C_{12}$ supplied by Stepan, Northfield, Ill., USA or Huntsman Corp. HLAS is acid form.

AES is $C_{12-14}$ alkyl ethoxy (3) sulfate, $C_{14-15}$ alkyl ethoxy (2.5) sulfate, or $C_{12-15}$ alkyl ethoxy (1.8) sulfate, supplied by Stepan, Northfield, Ill., USA or Shell Chemicals, Houston, Tex., USA.

AE is selected from $C_{12-13}$ with an average degree of ethoxylation of 6.5, $C_{11-16}$ with an average degree of ethoxylation of 7, $C_{12-14}$ with an average degree of ethoxylation of 7, $C_{14-15}$ with an average degree of ethoxylation of 7, or $C_{12-14}$ with an average degree of ethoxylation of 9, all supplied by Huntsman, Salt Lake City, Utah, USA.

AS is a $C_{12-14}$ sulfate, supplied by Stepan, Northfield, Ill., USA.

HSAS is mid-branched alkyl sulfate as disclosed in U.S. Pat. No. 6,020,303 and U.S. Pat. No. 6,060,443.

$C_{12-14}$ Dimethylhydroxyethyl ammonium chloride, supplied by Clariant GmbH, Germany.

$C_{12-14}$ dimethyl Amine Oxide is supplied by Procter & Gamble Chemicals, Cincinnati, USA.

Sodium tripolyphosphate is supplied by Rhodia, Paris, France.

Zeolite A is supplied by Industrial Zeolite (UK) Ltd, Grays, Essex, UK.

1.6R Silicate is supplied by Koma, Nestemica, Czech Republic.

Sodium Carbonate is supplied by Solvay, Houston, Tex., USA.

Acrylic Acid/Maleic Acid Copolymer is molecular weight 70,000 and acrylate:maleate ratio 70:30, supplied by BASF, Ludwigshafen, Germany.

PEG-PVAc polymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units. Available from BASF (Ludwigshafen, Germany).

Ethoxylated Polyethylenimine is a 600 g/mol molecular weight polyethylenimine core with 20 ethoxylate groups per —NH. Available from BASF (Ludwigshafen, Germany).

Zwitterionic ethoxylated quaternized sulfated hexamethylene diamine is described in WO 01/05874 and available from BASF (Ludwigshafen, Germany).

Grease Cleaning Alkoxylated Polyalkylenimine Polymer is a 600 g/mol molecular weight polyethylenimine core with 24 ethoxylate groups per —NH and 16 propoxylate groups per —NH. Available from BASF (Ludwigshafen, Germany).

Carboxymethyl cellulose is Finnfix® V supplied by CP Kelco, Arnhem, Netherlands.

Amylases (Natalase®, Stainzyme®, Stainzyme Plus®) may be supplied by Novozymes, Bagsvaerd, Denmark.

Savinase®, Lipex®, Celluclean™, Mannaway®, Pectawash®, and Whitezyme® are all products of Novozymes, Bagsvaerd, Denmark.

Proteases may be supplied by Genencor International, Palo Alto, Calif., USA (e.g. Purafect Prime®) or by Novozymes, Bagsvaerd, Denmark (e.g. Liquanase®, Coronase®).

Suitable Fluorescent Whitening Agents are for example, Tinopal® TAS, Tinopal® AMS, Tinopal® CBS-X, Sulphonated zinc phthalocyanine, available from BASF, Ludwigshafen, Germany.

Chelant is selected from, diethylenetetraamine pentaacetic acid (DTPA) supplied by Dow Chemical, Midland, Mich., USA, hydroxyethane diphosphonate (HEDP) supplied by Solutia, St Louis, Mo., USA; Ethylenediamine-N,N'-disuccinic acid, (S,S) isomer (EDDS) supplied by Octel, Ellesmere Port, UK, Diethylenetriamine penta methylene phosphonic acid (DTPMP) supplied by Thermphos, or1,2-dihydroxybenzene-3,5-disulfonic acid supplied by Future Fuels Batesville, Ark., USA Hueing agent is Direct Violet 9 or Direct Violet 99, supplied by BASF, Ludwigshafen, Germany.

Soil release agent is Repel-o-tex® PF, supplied by Rhodia, Paris, France.

Suds suppressor agglomerate is supplied by Dow Corning, Midland, Mich., US.

***Suds suppressor derived from phenylpropylmethyl substituted polysiloxanes, as described in the specification.

Acusol 880 is supplied by Dow Chemical, Midland, Mich., USA

TAED is tetraacetylethylenediamine, supplied under the Peractive® brand name by Clariant GmbH, Sulzbach, Germany.

Sodium Percarbonate supplied by Solvay, Houston, Tex., USA.

NOBS is sodium nonanoyloxybenzenesulfonate, supplied by Future Fuels, Batesville, Ark., USA.

What is claimed is:

1. A composition comprising from about 10% to about 50% by weight of a surfactant, a solvent comprising an ethoxylated diol of formula (I)

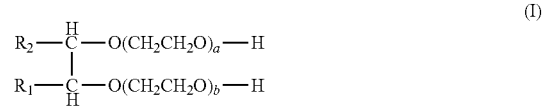

wherein each of $R_1$ and $R_2$ is independently selected from a substituted or unsubstituted, linear or branched, saturated or unsaturated $C_1$-$C_6$ alkyl group, and a+b has an average value of greater than 0 and less than or equal to about 20, an adjunct, and water, wherein said adjunct comprises from about 0.001% to about 1%, by weight of the composition, of enzyme, and wherein said adjunct further comprises a member selected from the group consisting of a structurant, a builder, an organic polymeric compound, an enzyme stabilizer, a bleach system, a brightener, a hueing agent, a chelating agent, a suds suppressor, a conditioning agent, a humectant, a perfume, a perfume microcapsule, a filler or carrier, an alkalinity system, a pH control system, a buffer, an alkanolamine, and mixtures thereof.

2. A composition comprising from about 30% to about 75% by weight of an anionic surfactant, wherein said anionic surfactant is a linear or branched alkoxylated alkyl sulfate, a solvent comprising an ethoxylated diol of formula (I)

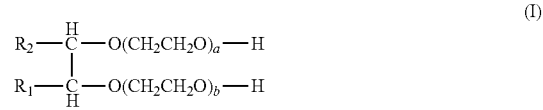

wherein each of $R_1$ and $R_2$ is independently selected from a substituted or unsubstituted, linear or branched, saturated or unsaturated $C_1$-$C_6$ alkyl group, and a+b has an average value of greater than 0 and less than or equal to about 20, and water.

3. The composition according to claim 1 wherein said solvent further comprises a monoalcohol of formula (II)

wherein each of $R_3$, $R_4$, and $R_5$ is independently selected from H or a substituted or unsubstituted, linear or branched $C_1$-$C_6$ alkyl group, glycerine, propoxylated glycerine, ethoxylated glycerine, propylene glycol, diethylene glycol, dipropylene glycol, or mixtures thereof.

4. The composition according to claim 1 wherein said surfactant is selected from the group consisting of anionic surfactant, cationic surfactant, nonionic surfactant, amphoteric surfactant, zwitterionic surfactant, and mixtures thereof.

5. The composition according to claim 4 wherein said anionic surfactant is selected from the group consisting of linear or branched alkyl benzene sulfonates, linear or branched alkoxylated alkyl sulfates, linear or branched alkyl sulfates, methyl ester sulfonates, paraffin sulfonates, α-olefin sulfonates, internal olefin sulfonates, and mixtures thereof.

6. The composition according to claim 5 wherein said anionic surfactant is a 2-alkyl branched primary alkyl sulfate.

7. The composition according to claim 1 wherein said composition comprises less than about 20% water.

8. The composition according to 1 wherein said enzyme is selected from the group consisting of lipase, amylase, protease, mannanase, cellulase, pectinase, and mixtures thereof.

9. The composition according to claim 1 wherein said composition is a form selected from the group consisting of a liquid laundry detergent, a gel detergent, a single-phase or multi-phase unit dose detergent, a detergent contained in a single-phase or multi-phase or multi-compartment water-soluble pouch, a liquid hand dishwashing composition, a laundry pretreat product, a fabric softener composition, and mixtures thereof.

10. The composition according to claim 9 wherein said composition is a detergent contained in a single-phase or multi-phase or multi-compartment water-soluble pouch.

11. A process for manufacturing an aqueous liquid or gel-form laundry detergent comprising the steps of:
(i) at a first location, preparing a shippable anionic surfactant paste comprising:
from about 30% to about 75% by weight of anionic surfactant, wherein said anionic surfactant is a linear or branched alkoxylated alkyl sulfate,
from about 3% to about 18% by weight of a solvent comprising an ethoxylated diol of formula (I)

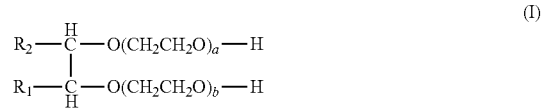

wherein each of $R_1$ and $R_2$ is independently selected from a substituted or unsubstituted, linear or branched, saturated or unsaturated $C_1$-$C_6$ alkyl group, and a+b has an average value of greater than 0 and less than or equal to about 20, and water;
(ii) shipping the anionic surfactant paste to a second location;
(iii) at the second location, adding said anionic surfactant paste to a composition comprising a surfactant and adjuncts.

* * * * *